(12) United States Patent
Liu et al.

(10) Patent No.: US 8,877,943 B2
(45) Date of Patent: Nov. 4, 2014

(54) RADIOTRACER PRECURSOR AND METHOD FOR PREPARING THE SAME

(75) Inventors: Show-Wen Liu, Taoyuan County (TW); Yu Chang, Taoyuan County (TW); Cheng-Fang Hsu, Taoyuan County (TW); Ming-Che Tsai, Taoyuan County (TW); Tsung-Hsien Chiang, Taoyuan County (TW); Yueh-Feng Deng, Taoyuan County (TW); Kuei-Lin Lu, Taoyuan County (TW); Chih-Yuan Lin, Taoyuan County (TW); Da-Ming Wang, Taoyuan County (TW); Ching-Yun Li, Taoyuan County (TW)

(73) Assignee: Atomic Energy Council-Institute of Nuclear Eenergy Research, Taoyuan County (TW)

( * ) Notice: Subject to any disclaimer, the term of this patent is extended or adjusted under 35 U.S.C. 154(b) by 135 days.

(21) Appl. No.: 13/609,938

(22) Filed: Sep. 11, 2012

(65) Prior Publication Data
US 2014/0073803 A1    Mar. 13, 2014

(51) Int. Cl.
*C07D 207/09*    (2006.01)
(52) U.S. Cl.
CPC .................................... *C07D 207/09* (2013.01)
USPC ........................................................ 548/402

(58) Field of Classification Search
None
See application file for complete search history.

(56) References Cited

FOREIGN PATENT DOCUMENTS

EP          317873 A1 *   5/1989

OTHER PUBLICATIONS

Hank F. Kung, Ravindra Kasliwal, Sangren Pan, Mei-Ping Kung, Robert H. Mach, and Yu-Zhi Guo; Dopamine D-2 Receptor Imaging Radiopharmaceuticals: Synthesis, Radiolabeling, and in Vitro Binding of (R)-(+)-and (S)-(-)-3-lodo-2-hydroxy-6-methoxy-N-[(1-ethyl-2-pyrrolidinyl)methyl]benzamide; J. Med. Chem. 1988, 31., 1039-1043.

* cited by examiner

*Primary Examiner* — Michael Barker
(74) *Attorney, Agent, or Firm* — Rosenberg, Klein & Lee

(57) ABSTRACT

A precursor SnBZM for a dopamine receptor radiotracer and a method for preparing the same are revealed. The precursor includes a tributyltin group ($Bu_3Sn$) that is easy to be replaced. Thus a dopamine receptor radiotracer $^{123}$I-IBZM can be produced at high yield rate by a substitution reaction of the precursor. At the same time, both the method for preparing the precursor SnBZM and a method for preparing a reference standard IBZM are simplified. Moreover, stability of each product is improved.

9 Claims, 5 Drawing Sheets

RADIOTRACER PRECURSOR AND METHOD FOR PREPARING THE SAME

BACKGROUND OF THE INVENTION

1. Fields of the Invention

The present invention relates to a radiotracer precursor and a method for preparing the same, especially to a radiotracer precursor containing a functional group of $Bu_3Sn$ and used to produce a dopamine receptor radiotracer.

2. Descriptions of Related Art

The Parkinson's disease causes a far greater burden in terms of economic and social cost to developed countries. In the people over age 65, there are about 15 percent of the people at risk of developing Parkinson's disease. Older people are even more likely to develop Parkinson's disease than younger people. The patients suffer from the loss of muscle function and mobility. Parkinson's disease has a great impact on both the sufferers and their caregiver.

The symptoms of Parkinson's disease result from the death of dopamine-generating cells in the midbrain and insufficient formation and activity of dopamine in certain neurons. Radiopharmaceuticals for imaging of dopamine receptors have been proven to be simple but powerful tools for differential diagnosis of Parkinson's and other neurodegenerative diseases. In order to diagnose diseases related to neural abnormality in the dopamine system, various radiopharmaceuticals for dopamine system imaging have been developed.

Dopamine D2/D3 receptors are distributed on dopaminergic postganglionic neurons and functioning in neurotransmission. The most common radio-imaging pharmaceuticals for binding D2/D3 receptor include $^{123}$I-IBZM($^{123}$I-iodobenzamide) or $^{11}$C-raclopride. In research of the recent decade, $^{123}$I-IBZM is widely used as a D2 receptor imaging agent. $^{123}$I-IBZM is usually used to evaluate neuro-degenerative diseases such as Parkinson's disease, Wilson's disease, Huntington's disease, etc. $^{123}$I-IBZM is the first radiopharmaceutical successfully used for imaging of D2 dopamine receptor in clinical, revealed in the paper "Dopamine D-2 Receptor Imaging Radiopharmaceuticals: Synthesis, Radiolabeling, and in Vitro Binding of (R)-(+)- and (S)-(−)-3-Iodo-2-hydroxy-6-methoxy-N-[(1-ethyl-2-pyrrolidinyl)methyl]benzamide *Journal of Medicinal Chemistry,* 1988, Vol. 31, No. 5, p. 1039", University of Pennsylvania, Kung et al., 1988. The structure of the $^{123}$I-IBZM is associated with benzamide. The $^{123}$I-IBZM is a dopamine antagonist, and is binding to the D2 receptor specifically. The $^{123}$I (iodine-123) is used in nuclear medicine imaging. There is only a very small amount of $^{123}$I-IBZM used in imaging so that the $^{123}$I-IBZM will not have pharmacological effect on users.

Refer to FIG. 1, $^{123}$I-IBZM is prepared by radioiodination of BZM [(S)-(−)-2-hydroxy-6-methoxy-N-[(1-ethyl-2-pyrrolidinyl)methyl]benzamide] with Iodine-123 in the presence of a buffer solution containing at least one oxidant. The buffer solution can be a phosphate buffer solution (pH 3) or ammonium acetate buffer solution (pH 4). The oxidant includes Chloramine T, hydrogen peroxide, and peracetic acid. However, the labeling yield and the radiochemical yield of such preparing method are unstable. Each batch has different products with great variations. This causes troubles in routine production.

Moreover, the method for preparing $^{123}$I-IBZM revealed by Kung et al has certain shortcomings. Refer to FIG. 2, it firstly produce a compound (2) by compound DMBA. Then get a compound (3) by an iodination reaction. Yet the compound (3) includes a carboxylic group. When the compound (3) is activated by thionyl chloride to form acid chloride, the carboxyl group may also react to give esters besides an amidation reaction can be carried out. Thus the yield rate is reduced. Therefore such method is not reliable.

SUMMARY OF THE INVENTION

Therefore it is a primary object of the present invention to provide a radiotracer precursor that is easy to react with iodide ions in solution and carry out a substitution reaction for producing a dopamine receptor radiotracer $^{123}$I-IBZM with higher yield rate. At the same time, the produced dopamine receptor radiotracer can be separated and purified easier.

It is another object of the present invention to provide a radiotracer precursor and a method for preparing the same by which steps for preparing reference standard IBZM and its precursor SnBZM are simplified. Thus the preparation of the radiotracer is more convenient and the yield rate is increased.

It is a further object of the present invention to provide a radiotracer precursor and a method for preparing the same that are applied to produce a dopamine receptor radiotracer $^{123}$I-IBZM. The yield rate of each batch is high and the quality is stable. Compared with conventional $^{123}$I-IBZM synthesized by BZM, the present invention has better production efficiency and quality.

In order to achieve the above objects, a method for preparing a radiotracer precursor of the present invention includes a plurality of steps. Firstly, synthesize a compound BZM. Then use the compound BZM and bromine chloride to carry out an iodination reaction for synthesis of a compound IBZM. Next take the compound IBZM and bis(tributyltin) in triethylamine solution to carry out a substitution reaction and get a compound SnBZM that is a radiotracer precursor. According to these steps, the radiotracer precursor SnBZM is prepared easily and efficiently.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

In order to solve the problems occurred during production of the dopamine receptor radiotracer $^{123}$I-IBZM such as poor yield rate and unstable final products, the present invention provides a precursor of the radiotracer $^{123}$I-IBZM, and a method for preparing the same.

Figure 1:
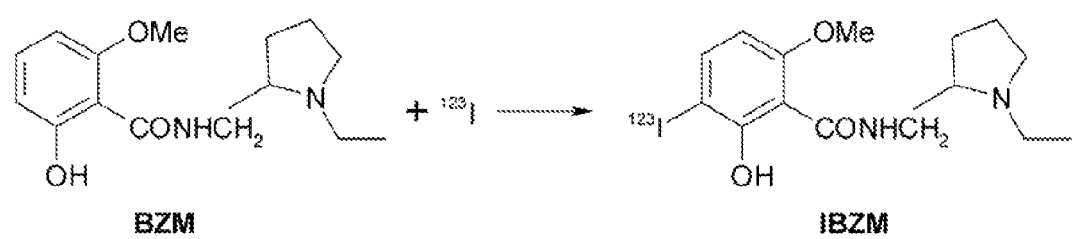
FIG. 1 is a schematic diagram showing the synthesis of $^{123}$I-IBZM of a prior art.
Figure 2:
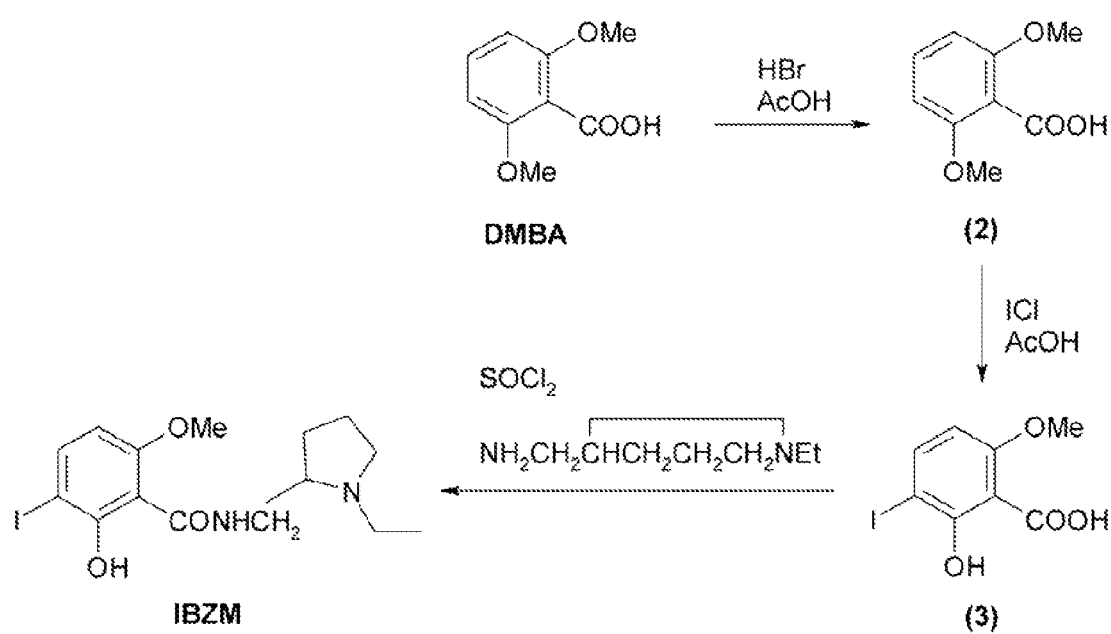
FIG. 2 is a schematic diagram showing the synthesis of IBZM of a prior art.
Figure 3:
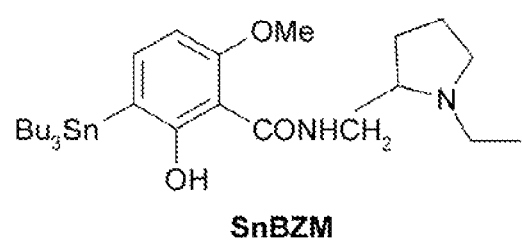
FIG. 3 shows a chemical structure of SnBZM of an embodiment according to the present invention.

Refer to FIG. 3, the chemical structure of a radiotracer precursor of the present invention is revealed. The radiotracer precursor includes a tributyltin group ($Bu_3Sn$) that is easy to be released. Thus the tributyltin group can be replaced easily by an iodide ion to form a final product $^{123}$I-IBZM. The reason the tributyltin group ($Bu_3Sn$) is easier to be released than a hydrogen group is that the tributyltin group includes more carbons, having lower polarity and higher solubility in solvents. That means it has a better solvent effect. Thus the $^{123}$I-IBZM produced by the substitution reaction has a better yield rate.

Figure 4:
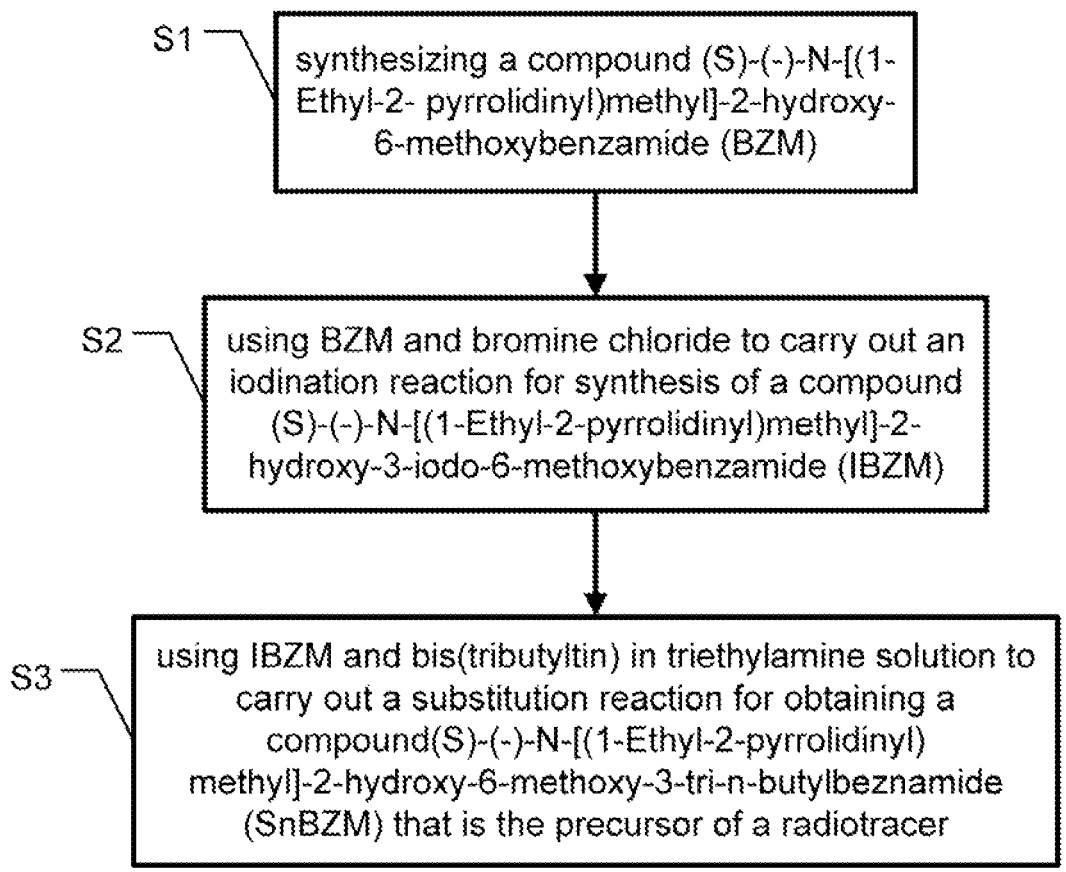
FIG. 4 is a flow chart showing steps of preparing SnBZM of an embodiment according to the present invention.

Refer to FIG. 4, a method for preparing a radiotracer precursor of the present invention includes following steps:
Step S1: synthesizing a compound BZM;
Step S2: using the compound BZM and bromine chloride to carry out an iodination reaction for synthesis of a compound IBZM; and
Step S3: using the compound IBZM and bis(tributyltin) in triethylamine solution to carry out a substitution reaction and get a compound SnBZM that is a radiotracer precursor.

Figure 5:
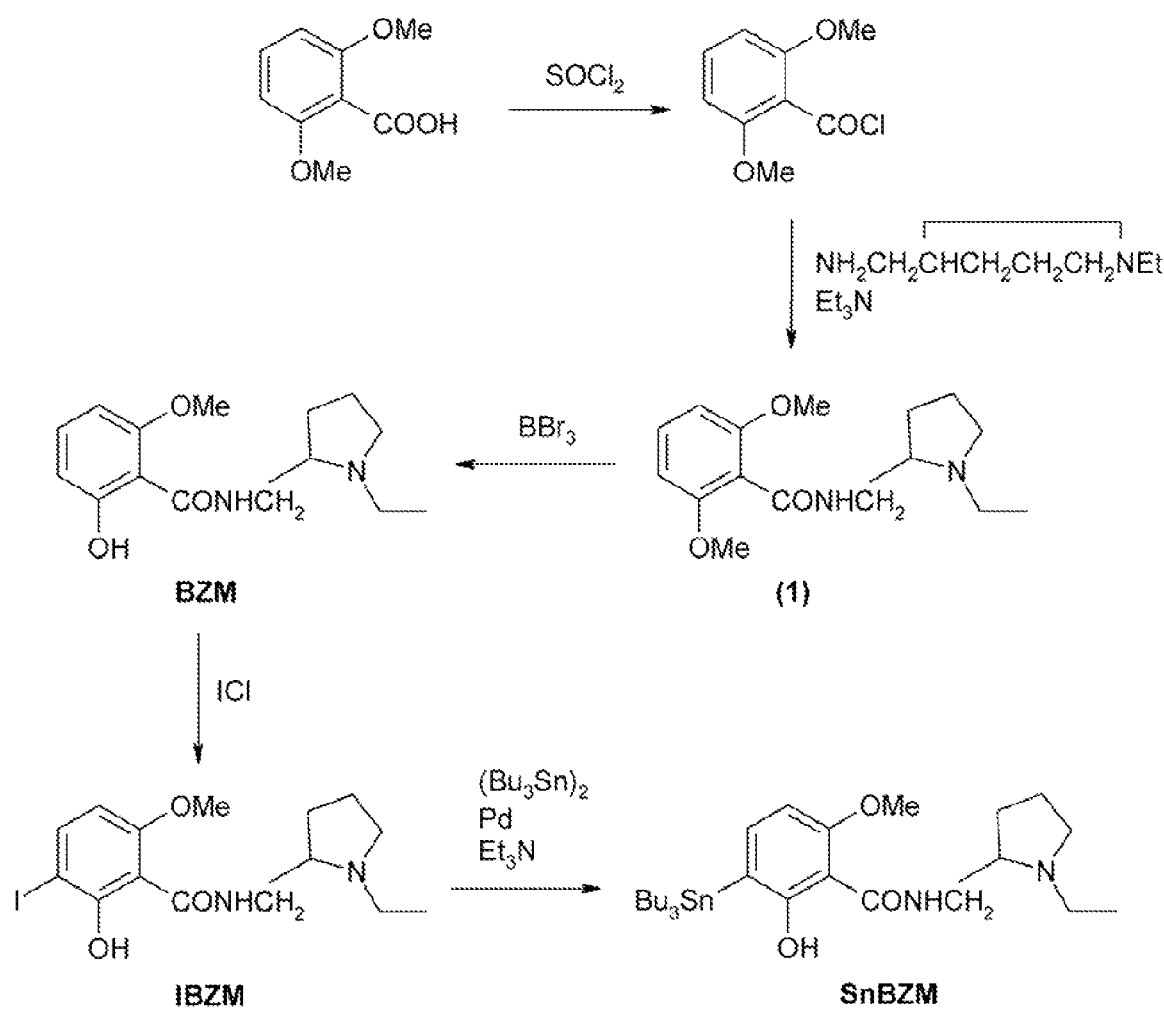
FIG. 5 is a schematic diagram showing the synthesis of SnBZM of an embodiment according to the present invention.

In the step S1, the compound (S)-(−)-N-[(1-Ethyl-2-pyrrolidinyl)-methyl]-2-hydroxy-6-methoxy benzamide (BZM) is firstly synthesized and a flow chart of the reactions is shown in FIG. 5. Some reactions of the preparation method are already known.

In the present invention, the preparation of the compound BZM includes a plurality of steps. Firstly, 2,6-Dimethoxybenzoic acid is activated by thionyl chloride and then is reacted with (S)-(−)-2-(aminomethyl)-1-methylpyrrolidine to carry out an amidation reaction at room temperature (about 25 degrees Celsius) for 24 hours and get a compound 1, (S)-(−)-N-[(1-Ethyl-2-pyrrolidinyl)-methyl]-2,6-dimethoxy benzamide.

During the preparation of BZM, the solvent used is hexane. Compared with the conventional solvents used including chloroform and dimethylformamide (DMF), the yield rate is improved from 81% to 84.5%.

Then use the synthesized compound (1) and boron tribromide ($BBr_3$) to carry out a demethylation reaction and produce the compound BZM. One of the methyl groups is removed so that a methoxy group is changed into a hydroxyl group and the compound BZM is obtained. The reaction temperature of demethylation is room temperature and the reaction time is 4 hours.

After production of BZM, use the compound BZM and bromine chloride to carry out an iodination reaction at 50° C. for 2 hours for synthesis of IBZM, (S)-(−)-N-[(1-Ethyl-2-pyrrolidinyl)-methyl]-2-hydroxyl-3-iodo-6-methoxy benzamide. The IBZM produced is non-radioactive $^{127}$I-IBZM, and is used as a reference standard to check whether BZM or the precursor BZM has been labeled and become $^{123}$I-IBZM by a thin layer chromatography (TLC) plate or high-performance liquid chromatography (HPLC) instrument. The IBZM obtained at this stage is directly synthesized by BZM and the yield rate is as high as 84.4%.

However, in order to make $^{123}$I stay in IBZM to form more stable $^{123}$I-IBZM, the IBZM obtained in the above step is used to prepare SnBZM in the present invention. That means the BZM is connected with a tributyltin group ($Bu_3Sn$) that is easy to be replaced. As the last reaction shown in FIG. 5, use the compound IBZM and bis(tributyltin)(($Bu_3Sn)_2$) in triethylamine solution ($Et_3N$) to carry out a substitution reaction. The iodo group is replaced by $Bu_3Sn$ to get the radiotracer precursor SnBZM. A catalyst is used in the substitution reaction. The catalyst can be bis(triphenylphosphine)palladium(II) dichlonide or tetrakis(triphenylphosphine)palladium(0) while the latter is preferred. The reaction temperature of the substitution reaction is 100° C. and the reaction time is ranging from 36 to 44 hours.

After formation of the radiotracer precursor SnBZM, uses can add radioactive isotope $^{123}$I into the precursor and get dopamine receptor radiotracer iodobenzamide $^{123}$I-IBZM by the substitution reaction in which tributyltin ($Bu_3Sn$) is replaced by the radioactive isotope $^{123}$I easily. The above process is not only simple and time-saving, and the yield rate is also excellent. Moreover, due to different physico-chemical properties of SnBZM and BZM, the efficiency of separation and purification is also improved. With less steps and stable yield rate, the radiotracer precursor SnBZM, IBZM and the method for preparing the same of the present invention is of high practical value.

The followings are details and related parameters of each step of embodiments according to the present invention.

Synthesis of Compound (1)

{(S)-(−)-N-[(1-Ethyl-2-pyrrolidinyl)methyl]-2,6-dimethoxybenzamide}

Take 2.8 g (15.4 mmol) 2,6-dimethoxybenzoic acid and add with 20 mL hexane and 2.4 mL (33.3 mmol) thionyl chloride. Heat and reflux for 2 hours and evaporate all volatile substances under reduced pressure. Then dissolve the residue in methylene chloride (20 mL) and slowly drop 20 mL methylene chloride containing 2.0 g (15.6 mmol) (S)-(−)-2-aminomethyl-1-ethylpyrrolidine into the methylene chloride solution. Stir the solution at room temperature overnight. Next wash the reaction solution with saturated sodium bicarbonate aqueous solution (40 mL) and the reaction solution separates into two phases. The organic phase is dried by anhydrous sodium sulfate ($Na_2SO_4$) and then is concentrated under reduced pressure. The residue is separated and purified by liquid chromatography (silicon dioxide($SiO_2$), dichloromethane($CH_2Cl_2$): methanol($CH_3OH$)=100:15) to get colorless solid product, the compound (1) (3.8 g, 84.5%).
Compound data of the product:
IR (KBr) ν 3324 (NH), 1663 (CO) $cm^{-1}$.
$^1$H NMR ($CDCl_3$) δ 7.15 (t, J=8.4 Hz, 1 H, Ph), 6.45 (d, J=8.4 Hz, 2 H, Ph), 6.32 (br, 1 H, NH), 3.69 (m, 7 H, $OCH_3$ and $NHCH_2$), 3.16 (m, 1 H, $NHCH_2$), 3.03 (m, 1 H, $CH_2CH_2CH_2N$), 2.77 (m, 1 H, $CH_2CH_3$), 2.57 (m, 1 H, CH), 2.11 (m, 2 H, $CH_2CH_3$ and $CH_2CH_2CH_2N$), 1.84-1.58 (m, 3 H, $CH_2CH_2CH_2N$), 0.99 (t, J=7.4 Hz, 3 H, $CH_2CH_3$). $^{13}$C NMR ($CDCl_3$) δ 165.19 (CO), 156.26, 129.36, 115.29 and 102.92 (Ph), 61.72 (CH), 54.79 ($OCH_3$), 52.47 ($CH_2$), 47.05 ($CH_2$), 39.53 ($CH_2$), 26.70 ($CH_2$), 21.70 ($CH_2$), 21.70 ($CH_2$), 12.60 ($CH_3$). MS m/z 292 ($M^+$), 264 ($M^+$-$CH_2CH_3$+1), 195 ($M^+$-$CH_3CH_2N(CH_2)_3CH$+1), 165 ($M^+$-$CH_3CH_2N(CH_2)_3CHCH_2N$), 98 (($CH_3CH_2N$—$(CH_2)_3CH)^+$).

Synthesis of BZM

{(S)-(−)-N-[(1-Ethyl-2-pyrrolidinyl)methyl]-2-hydroxy-6-methoxybenzamide}

Dissolve the compound (1) (0.94 g, 3.2 mmol) in 10 mL methanol. Then drop concentrated hydrochloric acid (0.6 mL, 7.2 mmol) into the solution, stir the solution well, and evaporate all volatile substances under reduced pressure. Next dissolve the residue in methylene chloride (30 mL), dry by anhydrous sodium sulfate and add with boron tribromide (0.96 g, 3.8 mmol).

Stir the mixture at room temperature for 4 hours and wash the reacted solution with 2N ammonium hydroxide aqueous solution (30 mL). After the solution separating into two phases, wash the water phase with methylene chloride (2×20 mL). The organic phase is dried by using anhydrous sodium sulfate and is concentrated under reduced pressure. Then the residue is separated and purified by liquid chromatography ($SiO_2$, $CH_2Cl_2$:$CH_3OH$=100:15) to get oily product BZM (0.62 g, 69.7%).

Compound data of the product:

IR (neat) v 3341 (NH), 1637 (CO) cm$^{-1}$. $^1$H NMR (CDCl$_3$) δ 8.92 (br, 1 H, NH), 7.18 (t, J=8.4 Hz, 1 H, Ph), 6.52 (d, J=8.4 Hz, 1 H, Ph), 6.31 (d, J=8.4 Hz, 1 H, Ph), 3.86 (s, 3 H, OCH$_3$), 3.64 (m, 1 H, NHCH$_2$), 3.24 (m, 2 H, NHCH$_2$ and NCH$_2$(CH$_2$)$_2$), 2.79 (m, 2 H, CH$_2$CH$_3$ and CH), 2.27 (m, 2 H, CH$_2$CH$_3$ and NCH$_2$(CH$_2$)$_2$), 1.90 (m, 1 H, CHCH$_2$CH$_2$), 1.71 (m, 2 H, CHCH$_2$CH$_2$), 1.59 (m, 1 H, CHCH$_2$CH$_2$), 1.09 (t, J=7.2 Hz, 3 H, CH$_3$CH$_2$). $^{13}$C NMR (CDCl$_3$) δ 170.34 (CO), 164.34, 158.83, 133.07, 111.42, 103.96 and 100.81 (Ph), 62.45 (CH), 55.94 (OCH$_3$), 53.64 (CH$_2$), 48.31 (CH$_2$), 40.70 (CH$_2$), 28.45 (CH$_2$), 22.95 (CH$_2$), 13.61 (CH$_3$). MS m/z 278 (M$^+$), 180 (M$^+$-CH$_3$CH$_2$N(CH$_2$)$_3$CH), 151 (M$^+$-CH$_3$CH$_2$N(CH$_2$)$_3$CHCH$_2$NH), 98 ((CH$_3$CH$_2$N(CH$_2$)$_3$C H)$^+$).

Synthesis of IBZM

{ (S)-(−)-N-[(1-Ethyl-2-pyrrolidinyl)methyl]-2-hydroxy-3-iodo-6-methoxybenzamide)}

Dissolve BZM (0.94 g, 3.4 mmol) in 60 mL absolute methanol solution. Add iodine monochloride (0.2 mL, 3.8 mmol) into the solution and heat at 50 degrees Celsius for 2 hours. Evaporate all volatile substances under reduced pressure. Then dissolve the residue in 50 mL methylene chloride and wash with 2N sodium bisulfite aqueous solution (50 mL) to remove residual iodine. The organic phase is dried by anhydrous sodium sulfate and is concentrated under reduced pressure. Next the residue is separated and purified by liquid chromatography (SiO$_2$, CH$_2$Cl$_2$:CH$_3$OH=10:1) to get oil product IBZM (1.16 g, 84.4%).

Compound data of the product:

IR (neat) v 3334 (NH), 1636 (CO) cm$^{-1}$. $^1$H NMR (CDCl$_3$) δ 8.94 (br, 1 H, NH), 7.61 (d, J=8.7 Hz, 1 H, Ph), 6.18 (d, J=8.7 Hz, 1 H, Ph), 3.85 (s, 3 H, OCH$_3$), 3.60 (ddd, J=13.8, 6.9 and 3.3 Hz, 1 H, CH$_2$NH), 3.24 (m, 1 H, CH$_2$NH), 2.76 (m, 1 H, CH$_2$CH$_3$), 2.67 (m, 1 H, CH), 2.20 (m, 2 H, CH$_2$CH$_3$ and NCH$_2$(CH$_2$)$_2$), 1.85 (m, 1 H, CHCH$_2$CH$_2$), 1.67 (m, 2 H, CHCH$_2$CH$_2$), 1.51 (m, 1 H, CHCH$_2$CH$_2$), 1.06 (t, J=7.2 Hz, 3 H, CH$_3$CH$_2$). $^{13}$C NMR (CDCl$_3$) δ 169.45 (CO), 162.49, 159.03, 141.63, 104.17, 103.10 and 76.86 (Ph), 61.94 (CH), 56.14 (OCH$_3$), 53.44 (CH$_2$), 47.94 (CH$_2$), 40.74 (CH$_2$), 28.30 (CH$_2$), 22.84 (CH$_2$), 13.71 (CH$_3$CH$_2$). MS m/z 404 (M$^+$), 277 ((I(OH)(CO)(OCH$_3$)C$_6$H$_2$)$^+$), 98 ((CH$_3$CH$_2$N(CH$_2$)$_3$CH)$^+$).

Synthesis of SnBZM

{ (S)-(−)-N-[(1-Ethyl-2-pyrrolidinyl)methyl]-2-hydroxy-6-methoxy-3-tri-n-butylbeznamide)}

Take IBZM (0.52 g, 1.29 mmol), bis(tributyltin)(2.4 mL, 4.8 mmol), tetrakis(triphenyl-phosphine) palladium(0), and triethylamine (6 mL) into a pressure flask. After air being removed by freeze-pump-thaw cycles, the flask is sealed in liquid nitrogen and then is heated at 100 degrees Celsius for 36-44 hours. During the process, pay attention to the pressure flask for safety. After being cooled down, dissolve the reactants in 20 mL hexane. The solution is filtered and then concentrated under reduced pressure. Next the residue is separated and purified by liquid chromatography (SiO$_2$, CH$_2$Cl$_2$:CH$_3$OH=100:10 and CH$_2$Cl$_2$:Etoad=100:10) so as to get oily product SnBZM (0.26 g, 35.4%).

Compound data of the product:

IR (neat) v 3332 (NH), 1622 (CO) cm$^{-1}$ H NMR (CDCl$_3$) δ 9.04 (br, 1 H, NH), 7.29 (d, J=8.1 Hz, 1 H, Ph), 6.38 (d, J=7.8 Hz, 1 H, Ph), 3.95 (s, 3 H, OCH$_3$), 3.79 (m, 1 H, CH$_2$NH), 3.54 (m, 2 H, CH$_2$NH and CH$_2$(CH$_2$)$_2$CH), 3.30 (br, 1 H, CH), 3.01 (m, 1 H, CH$_2$CH$_3$), 2.61 (m, 1 H, CH$_2$CH$_3$), 2.50 (m, 1 H, CH$_2$(CH$_2$)$_2$CH), 2.03 (m, 1 H, CHCH$_2$CH$_2$), 1.87 (m, 2 H, CHCH$_2$CH$_2$), 1.71 (m, 1 H, CHCH$_2$CH$_2$), 1.48 (m, 6 H, CH$_2$ of butyl), 1.26 (m, 9 H, CH$_3$ of ethyl and CH$_2$ of butyl), 0.99 (m, 6 H, CH$_2$ of butyl), 0.82 (t, J=7.1 Hz, 9 H, CH$_3$ of butyl). $^{13}$C NMR (CDCl$_3$) δ 171.21 (CO), 168.33, 159.57, 141.15, 122.44, 102.42 and 101.53 (Ph), 64.33 (CH), 56.30 (OCH$_3$), 54.03 (CH$_2$), 49.86 (CH$_2$), 40.87 (CH$_2$), 29.02 (CH$_2$ of butyl), 28.55 (CH$_2$), 27.25 (CH$_2$ of butyl), 23.09 (CH$_2$), 13.60 (CH$_2$ of butyl), 12.30 (CH$_3$CH$_2$) 9.59 (CH$_3$ of butyl). MS m/z 511 and 509 (M$^+$-(CH$_2$)$_3$CH$_3$), 383 and 381 (M$^+$-(CH$_2$)$_3$CH$_3$—CH$_3$CH$_2$N(CH$_2$)$_3$CH-2CH$_3$).

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A precursor of a radiotracer is represented by the following structural formula:

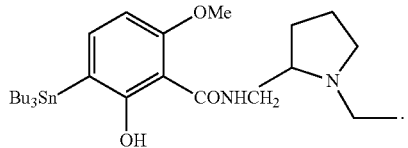

2. The precursor as claimed in claim 1, the radiotracer is a dopamine receptor radiotracer.

3. A method for preparing a precursor of a radiotracer comprising the steps of:
   synthesizing a compound (S)-(−)-N-[(1-Ethyl-2-pyrrolidinyl)methyl]-2-hydroxy-6-methoxybenzamide (BZM);
   using BZM and bromine chloride to carry out an iodination reaction for synthesis of a compound (S)-(−)-N-[(1-Ethyl-2-pyrrolidinyl)methyl]-2-hydroxy-3-iodo-6-methoxybenzamide (IBZM); and
   using IBZM and bis(tributyltin) in triethylamine solution to carry out a substitution reaction for obtaining a compound (S)-(−)-N-[(1-Ethyl-2-pyrrolidinyl) methyl]-2-hydroxy-6-methoxy-3-tri-n-butylbenzamide (SnBZM) that is the precursor of a radiotracer and having a structural formula of:

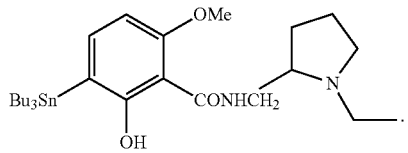

4. The method as claimed in claim 3, wherein the step of synthesizing BZM further includes the steps of:
   using 2,6-Dimethoxybenzoic acid activated by thionyl chloride to react with (S)-(−)-2-(aminomethyl)-1-methyl-pyrrolidine and carry out an amidation reaction for producing a compound (S)-(−)-N-[(1-Ethyl-2-pyrrolidinyl)-methyl]-2,6-dimethoxy benzamide; and
   using use (S)-(−)-N-[(1-Ethyl-2-pyrrolidinyl)-methyl]-2,6-dimethoxy benzamide and boron tribromide ((BBr3)) to carry out a demethylation reaction and get the BZM.

5. The method as claimed in claim 4, wherein in the amidation reaction, reaction temperature is room temperature and reaction time is 24 hours.

6. The method as claimed in claim 4, wherein in the demethylation reaction, reaction temperature is room temperature and reaction time is 4 hours.

7. The method as claimed in claim 3, wherein in the iodination reaction, reaction temperature is 50 degrees Celsius and reaction time is 2 hours.

8. The method as claimed in claim 3, wherein in the substitution reaction, reaction temperature is 100 degrees Celsius and reaction time is ranging from 36 to 44 hours.

9. The method as claimed in claim 3, wherein a catalyst is used in the substitution reaction and the catalyst is selected from the group consisting of bis(triphenylphosphine)palladium(II) dichlonide and tetrakis(triphenylphosphine)palladium(0).

* * * * *